United States Patent [19]
Wang

[11] Patent Number: 5,733,297
[45] Date of Patent: Mar. 31, 1998

[54] CUTTER FOR SURGICAL PROBE

[75] Inventor: Carl C. T. Wang, Oakland, Calif.

[73] Assignee: Medical Instrument Development Laboratories, Inc., San Leandro, Calif.

[21] Appl. No.: 711,198

[22] Filed: Sep. 10, 1996

[51] Int. Cl.⁶ ................................................. A61B 17/32
[52] U.S. Cl. .............................................. 606/167; 606/170
[58] Field of Search ........................... 606/171, 170, 606/167, 159

[56] References Cited

U.S. PATENT DOCUMENTS

| | | | |
|---|---|---|---|
| 3,884,237 | 5/1975 | O'Malley et al. | 128/303.14 |
| 3,884,238 | 5/1975 | O'Malley et al. | 128/305 |
| 4,011,869 | 3/1977 | Seiler, Jr. | 606/171 |
| 4,099,529 | 7/1978 | Peyman | 128/305 |
| 4,167,943 | 9/1979 | Banko | 128/305 |
| 4,167,944 | 9/1979 | Banko | 128/305 |
| 4,324,243 | 4/1982 | Helfgott et al. | 128/276 |
| 4,696,298 | 9/1987 | Higgins et al. | 128/305 |
| 4,819,635 | 4/1989 | Shapiro | 128/305 |
| 4,850,354 | 7/1989 | McGurk-Burleson et al. | 128/305 |
| 4,909,249 | 3/1990 | Akkas et al. | 606/107 |
| 5,047,008 | 9/1991 | de Juan, Jr. et al. | 604/22 |
| 5,100,426 | 3/1992 | Nixon | 606/170 |
| 5,106,364 | 4/1992 | Hayafuji et al. | 606/171 |
| 5,275,609 | 1/1994 | Pingleton et al. | 606/170 |
| 5,324,301 | 6/1994 | Drucker | 606/180 |
| 5,346,497 | 9/1994 | Simon et al. | 606/107 |
| 5,474,532 | 12/1995 | Steppe | 604/32 |
| 5,487,725 | 1/1996 | Peyman | 304/22 |

Primary Examiner—Michael Buiz
Assistant Examiner—Kevin Truong
Attorney, Agent, or Firm—Godfrey & Kahn, S.C.

[57] ABSTRACT

A cutter for use in a surgical probe where the cutter has a first end for being coupled to a driving mechanism and an opposite end on which a blade portion and a contact portion are formed. The cutter is formed from a tube of hard material, such as stainless steel. The contact portion extends beyond the blade portion, which is used to cut tissue, thereby preventing the blade portion from contacting or hitting the inner surface of the closed end or tip of the needle of the probe.

12 Claims, 2 Drawing Sheets

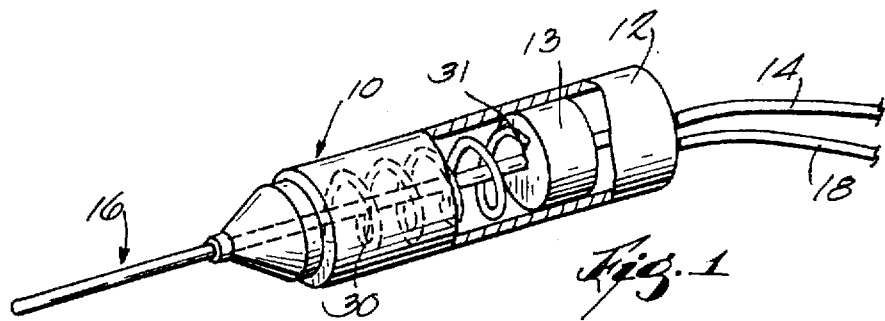
Fig. 1
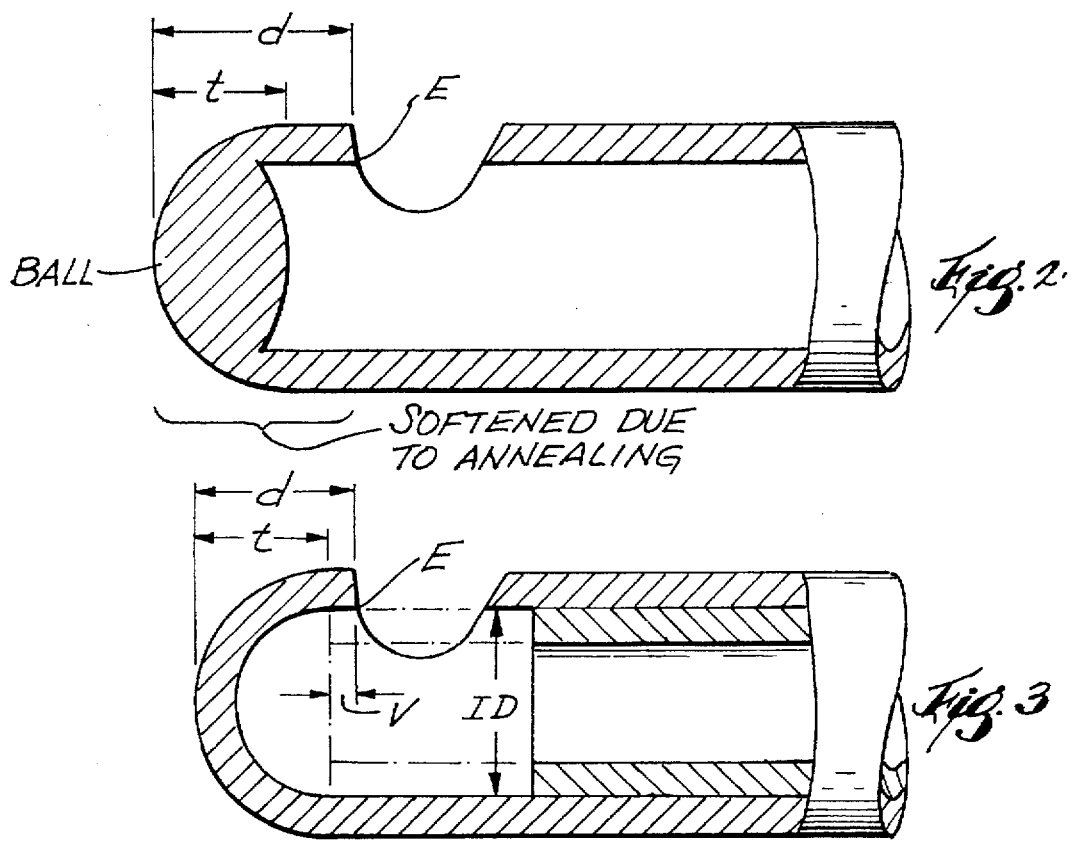
Fig. 2 — SOFTENED DUE TO ANNEALING
Fig. 3 — ID = INNER DIAMETER; t = THICKNESS OF TIP; V = MAX. OVERTRAVEL; d = t + V
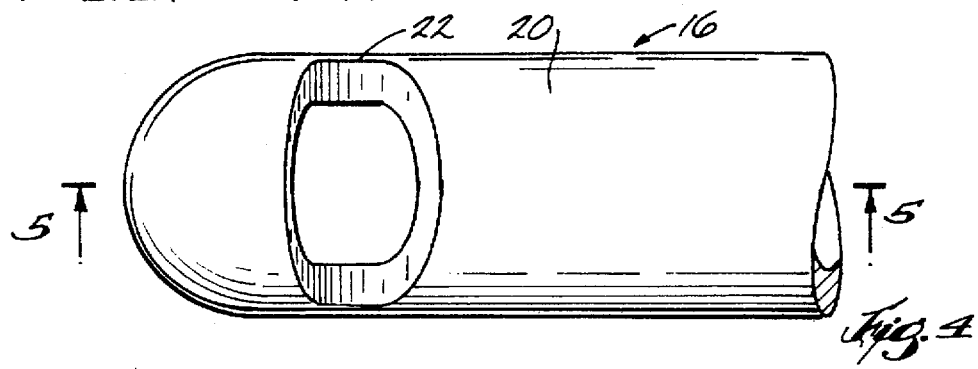
Fig. 4

CUTTER FOR SURGICAL PROBE

BACKGROUND OF THE INVENTION

The present invention relates to surgical probes used for vitrectomies and similar surgical procedures. More particularly, the present invention relates to a cutter for use in a surgical probe where the cutter design allows the cutting port to be placed very close to the probe tip.

Microsurgical cutting probes have been used for many years to perform surgical procedures such as vitrectomies, where the vitreous humor, a material containing many fine collagen fibrils, is excised from the eye. Other procedures such as arthroscopic surgeries use similar probes to excise cartilage and other tissue. One class of microsurgical probes is designed on the principle of automated biopsy devices. These instruments have a front section which includes an outer tube, frequently referred to as a needle, with a closed end. Near the closed end is a cutting port or aperture. Within the needle is a second tube, often referred to as a cutter. The cutter reciprocates within the needle.

The basic concept and operation of a microsurgical probe combines a constant suction force with a repeated cutting action of the cutter. Material is sucked into the aperture of the needle by the suction. As the material passes through the aperture, the reciprocating cutter, acting in cooperation with the edge of the aperture, cuts the tissue into small pieces which are removed by the suction to a collection device coupled to the probe.

During clinical use of these probes, it became apparent that positioning the aperture very near the closed end or tip of the needle results in improved efficacy of the probe in reaching to certain surgical sites. Thus, in vitrectomy probes the distance, d, (shown in FIG. 2) between the aperture and the probe tip has decreased from about 0.060 inches to about 0.025 inches. Hereinafter, this distance will be referred to as the "aperture offset."

Due to the manner in which needles of microsurgical probes are manufactured, there is a limitation to shortening the aperture offset (distance, d). The limitation is caused, in part, to the thickness, t, of the tip of the needle. The thickness, t, of the tip (hereinafter the "tip thickness") is dependent on how the end of the needle is created. To create the tip, one open end of the needle is closed, for example, by welding.

When the tip of the needle is closed by welding, a ball shaped plug is created in one of its ends, as is shown in FIG. 2. The heating and cooling process (annealing) undergone as a result of the welding process softens the end of the needle. The softening results in at least one problem. The aperture is formed in the softened end of the needle causing the front edge, E, of the aperture to be relatively soft. This results in a relatively poor cutting edge. As was discussed earlier, the edge of the aperture and the reciprocating cutter work together to shear or cut material sucked into the surgical probe. In order for the aperture to have a suitably hard front edge, E, it is necessary to move the aperture away from the softened end of the needle so that it is formed in a portion of the needle not significantly affected by the welding process. Generally, this means that the aperture offset (distance d) must be at least 0.020 inches for a 20 gauge stainless steel tube.

A tip on the needle may also be created by swaging. Swaging refers to crimping or bending cold metal to a desired shape. Swaging the end of the needle results in a probe tip having a profile like the probe shown in FIG. 3. The end of the needle is not softened since swaging is a cold process. That is, no heat is applied when the needle is swaged closed. To the contrary, the material of the needle may be hardened due to the cold forming process. Thus, the front edge, E, of the aperture may be placed relatively close to the tip.

With present techniques it is possible, using a 20 gauge tube, to produce a tip where the tip thickness (thickness t) is 0.0065 inches. Further, in a swaged closed, surgical probe it is possible to reduce the distance between the front edge of the aperture and the point at which the inner diameter of the needle decreases to form the tip. This distance, v, is the maximum distance the cutter can travel past the aperture before hitting the inner surface of the tip wall. Using present techniques, it may be possible to reduce the distance v to less than about 0.0055 inches on a 20 gauge tube.

The aperture offset (distance d) can be determined from the following equation:

$$d = t + v. \qquad \text{(Eqn. 1)}$$

For the example of using a 20 gauge tube, and as can be calculated by placing the values mentioned above into Eqn. 1, it is possible to construct a surgical probe having an aperture offset of less than about 0.012 inches, an improvement over the previously mentioned aperture offset of 0.025 inches or more.

To ensure effective cutting of vitreous material and other tissue, it has been observed, for a 20 gauge vitrectomy probe, that the cutter should have a minimum over travel (the distance the cutter travels past the aperture edge E) of at least 0.003 inches. Assuming this to be accurate, microsurgical probes should be constructed with an over travel of between about 0.003 inches to about 0.0055 inches, resulting in a tolerance of about 0.0025 inches. A tolerance this small is virtually impossible to achieve, except, perhaps, by using very expensive manufacturing techniques.

Because such a small tolerance is, using practical manufacturing procedures, unachievable, microsurgical probes constructed to have a small aperture offset will suffer from at least one serious problem. In particular, the over travel of the cutter will cause it to be driven into the inner surface of the needle. As can be appreciated, the cutting edge, referred to as the "blade," of the cutter will be damaged and dulled after hitting the inner surface of the tip repeatedly. In addition, damage to the tip may occur. Either of these events may require costly repair or replacement of the surgical probe.

Accordingly, it would be desirable to have an improved cutter for use in a surgical probe which is not dulled or damaged due to repeated contact with the inner surface of the probe tip wall. In addition, it would be desirable to have an improved cutter for use in a surgical probe which reduced the amount of damage to the inner surface of the tip of the needle caused by contact with the cutter.

OBJECTS AND SUMMARY OF THE INVENTION

Therefore, it is an object of the present invention to provide a cutter for a surgical probe having a means for preventing the blade of the cutter from hitting the inner surface of the tip of the needle.

A further object of the present invention is to provide a surgical probe having a cutter with a means for preventing the blade of the cutter from hitting the inner surface of the tip of the needle.

These and other objects are achieved in a cutter for use in a surgical probe where the cutter has a first end for being coupled to a driving mechanism and an opposite end on which a blade portion and a contact portion are formed. The cutter is formed from a tube of hard material, such as stainless steel. The contact portion extends beyond the blade portion, which is used to cut tissue, thereby preventing the blade portion from hitting the inner surface of the closed end or tip of the needle.

In one form of the present invention, the cutter is formed with a blade portion and a foot. The foot extends beyond the blade portion and prevents the blade portion from hitting the inner surface of the tip of the needle. In a second embodiment, the cutter is angularly shaped and has a contact portion that is longer than, or extends beyond, the blade portion of the cutter. The contact portion prevents the blade portion, which is positioned near the aperture, from hitting the inner surface of the tip of the needle.

The cutter is designed to be positioned coaxially with and telescoped within the needle or the outer tube. The outer tube has a wall, a closed end or tip with a concave inner surface, and an aperture formed in the wall near the tip. As noted above, the cutter has an end for being coupled to a driving mechanism and an opposite end with a blade portion and a contact portion. As the cutter is driven in a reciprocating fashion past the aperture in the outer tube, tissue such as vitreous material is cut. The cut material is sucked through the probe by a suction source coupled to the probe.

Further objects and advantages of the present invention will become more apparent from the following detailed description of the invention taken in combination with the accompanying drawings.

BRIEF DESCRIPTION OF THE DRAWINGS

FIG. 1 is a perspective view of an exemplary microsurgical probe.

FIG. 2 is cross sectional view of a needle tip formed by welding.

FIG. 3 is a cross sectional view of a needle tip formed by swaging and the end the cutter.

FIG. 4 is a top, plan view of a needle tip constructed according to a preferred embodiment of the present invention.

DETAILED DESCRIPTION OF THE INVENTION

Figure 5:
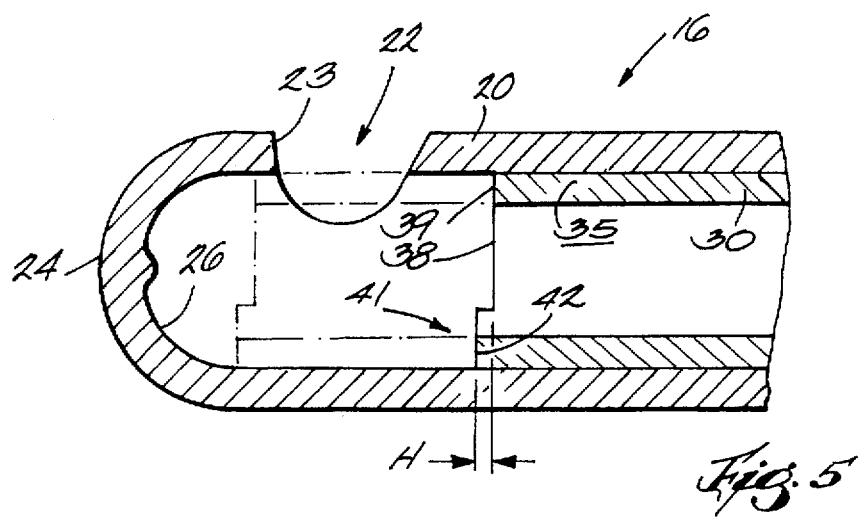
FIG. 5 is a longitudinal cross-sectional view of the microsurgical needle tip of FIG. 4 taken along the line 5—5 of FIG. 4, showing a cutter constructed according to a first embodiment of the present invention.

A surgical probe 10 is shown in FIG. 1. The surgical probe includes a housing 12. The housing 12 holds a driving mechanism 13 (shown schematically). In addition, the surgical instrument 10 is designed to be coupled to a source of suction through tubing 14 or the like and to a source of driving energy, such as a source of pneumatic energy, through tubing 18. It should be understood that the driving mechanism and source of suction are features known in the art and that the improved cutter of the present invention is designed to be used in connection with known reciprocating surgical instruments.

The surgical probe 10 also includes a front end 16. As best seen by reference to FIGS. 4, 5, and 6, the front end 16 includes an outer tube or needle 20 having an aperture 22 formed therein. The aperture has a leading edge 23.

The outer tube or needle 20 also has a tip 24 having a concave inner surface 26. As was discussed above, the tip 24 can be formed by swaging or other cold-work technologies. In the preferred embodiment, the needle is usually made from stainless steel and after the tip is created it may be ground and/or buffed, using techniques known in the art, to a desired shape chosen to facilitate insertion of the probe into tissue.

Telescoped within, and coaxial to, the needle 20 is an inner tube or cutter 30. The cutter 30 is manufactured from a relatively hard material, usually stainless steel, and is designed to reciprocate along its longitudinal axis in a forward and back direction. The cutter 30 has a first end 31 (FIG. 1) which is coupled to the driving mechanism 13. When activated, the driving mechanism 13 drives the second end discussed below of the cutter back and forth past the aperture 22.

The cutter 30 has a second end 35 on which an edge 38 having a blade portion 39 is formed. A contact portion 41 is formed on the opposite side of the edge 38. As can be seen by reference to FIG. 5, in one embodiment of the present invention the contact portion takes the form of a foot 42. The foot 42 extends beyond the blade portion 39. When the cutter 30 reciprocates within the needle 20, the blade portion 39 is driven past the aperture 22. As was noted earlier, it is not practical to have the probe made so precisely that the cutter 30 is driven past the leading edge 23 of the aperture 22 without the cutter edge 38 hitting the inner surface 26 of the tip 24. However, the foot 42 prevents the blade portion 39 from hitting the inner surface 26. In the preferred embodiment, using a 20 gauge vitrectomy probe as an example, the foot extends about 0.0025 inches beyond the blade portion 39 and has a height, H, of 0.0025 inches.

Figure 6:
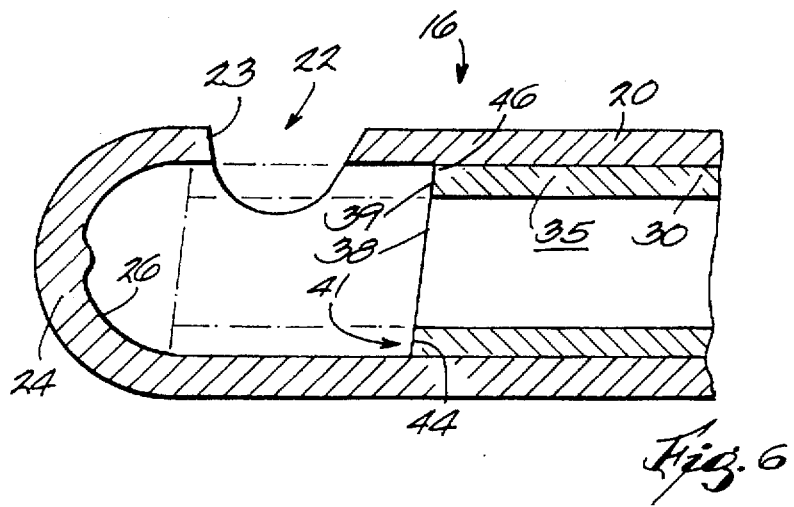
FIG. 6 is a view similar to FIG. 5, showing a cutter constructed according to a second embodiment of the present invention.
Figure 7:
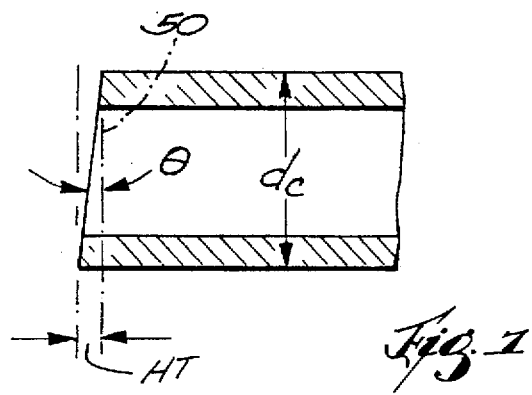
FIG. 7 is a view of the cutter of FIG. 6 shown outside of the needle.

As seen in FIG. 6, in a second embodiment of the present invention, the contact portion 41 takes the form of a leading edge 44. The leading edge 44 and a trailing edge 46 are formed by angling the second end 35 of the cutter 30. Angling the cutter 30 prevents the entire edge 38 from hitting the inner surface 26 when the cutter 30 is reciprocated in the needle 20. As seen in FIG. 7, a dotted line 50 shows the configuration of the edge 38 when the second end 35 of the cutter 30 is flat, or an angle of 90° is made. When the cutter is angled, the edge 38 should be offset from the line 50 by an angle $\theta$ of about 5.5°. The trigonometric calculation is based on achieving a desired height, HT, of about 0.0025 inches for a cutter having an outer diameter, $d_c$, of about 0.026 inches. When the cutter is properly angled, the contact portion 44 extends beyond the rest of the edge 38, thereby preventing the blade portion 39 from hitting the inner surface 26 of the tip 24 when the cutter 30 is in use.

In both embodiments, the contact portion 41 may be a relatively dull, rounded edge or be otherwise relatively dull so as to protect the inner surface 26 of the tip 24 from damage. Thus, in the first embodiment the foot 42 may be relatively dull. In the second embodiment, the leading edge 44 may be relatively dull.

Thus, the cutter 30 of the present invention allows the cutting port or aperture 22 to be placed very close to the probe tip, as the effects of contact between the inner surface of the needle tip and blade portion of the cutter are avoided due to the provision of a contact portion on the cutter.

While the present invention has been described in what is believed to be the most preferred forms, it is to be understood that the invention is not confined to the particular construction and arrangement of the components herein illustrated and described, but embraces such modified forms thereof as come within the scope of the appended claims. In particular, the present invention should not be limited to the particular example of a 20 gauge needle used in a vitrectomy probe.

What is claimed is:

1. A front end of a surgical probe comprising:

a first tube having a wall, a closed end with an inner surface, and an aperture formed in the wall near the closed end; and a second tube coaxial with and telescoped within the first tube and having a first end for being coupled to a driving mechanism and a second end with a blade portion for cutting tissue and a contact portion formed on the second end, adjacent and extending beyond to the blade, the contact portion for preventing the blade portion from contacting the inner surface of the closed end of the first tube.

2. A front end of a surgical probe as claimed in claim 1, wherein the second end of the second tube is angled.

3. A front end of a surgical probe as claimed in claim 2, wherein an extended first portion of the angled second end of the second tube is relatively dull compared to a shorter second portion of the angled second end of the second tube.

4. A front end of a surgical probe as claimed in claim 1, wherein the contact portion on the second end of the second tube is a foot which extends beyond the blade portion of the second end of the second tube.

5. A front end of a surgical probe as claimed in claim 1, wherein the foot extends about 0.0025 inches beyond the blade.

6. A front end of a surgical probe as claimed in claim 1, wherein the first tube and the second tube are manufactured from stainless steel.

7. A front end of a surgical probe as claimed in claim 1, wherein the aperture is about 0.025 inches from the closed end of the first tube.

8. A cutter for use with a surgical probe having a front portion, the front portion including a first tube with a wall, a closed end with an inner surface, and an aperture formed in the wall near the closed end, the cutter comprising:

a second tube capable of being coaxial with and telescoped within the first tube and having a first end for being coupled to a driving mechanism and a second end including a blade portion for cutting tissue and a non-cutting contact portion extending beyond the blade portion, the contact portion for preventing the blade portion from contacting the closed end of the first tube.

9. A cutter as claimed in claim 8, wherein the second end is angled.

10. A cutter as claimed in claim 9, wherein an extended first portion of the second end is relatively dull compared to a shorter second portion of the second end.

11. A cutter as claimed in claim 8, wherein the contact portion is a foot which extends beyond the blade portion.

12. A cutter as claimed in claim 8, wherein the first tube and the second tube are manufactured from stainless steel.

* * * * *

UNITED STATES PATENT AND TRADEMARK OFFICE
CERTIFICATE OF CORRECTION

PATENT NO. : 5,733,297
DATED : March 31, 1998
INVENTOR(S) : Carl C.T. Wang

It is certified that error appears in the above-indentified patent and that said Letters Patent is hereby corrected as shown below:

Col. 3, line 39, after "swaging" delete --and--.

Col. 5, line 16, delete "adjacent and extending beyond to" and substitute therefor --adjacent to and extending beyond--.

Col. 5, line 17, after "blade" insert --portion--.

Col. 6, line 3, after "blade" insert --portion--.

Signed and Sealed this

Fourteenth Day of July, 1998

Attest:

BRUCE LEHMAN

*Attesting Officer*            *Commissioner of Patents and Trademarks*